(12) United States Patent
Huang et al.

(10) Patent No.: US 10,631,813 B1
(45) Date of Patent: Apr. 28, 2020

(54) MULTI-POCKET CARRIER FOR X-RAY PHOTO-SENSITIVE PLATES AND SYSTEM AND METHOD OF USE

(71) Applicant: APIXIA Inc., Industry, CA (US)

(72) Inventors: Jerry Huang, Covina, CA (US); Peter Chen, Diamond Bar, CA (US); Ta-Ko Huang, Taipei (TW)

(73) Assignee: APIXIA INC, Industry, CA (US)

( * ) Notice: Subject to any disclaimer, the term of this patent is extended or adjusted under 35 U.S.C. 154(b) by 0 days.

(21) Appl. No.: 16/428,985

(22) Filed: Jun. 1, 2019

(51) Int. Cl.
*A61B 6/00* (2006.01)
*G06T 7/00* (2017.01)

(52) U.S. Cl.
CPC ............ *A61B 6/5241* (2013.01); *A61B 6/587* (2013.01); *G06T 7/0012* (2013.01); *G06T 2207/10116* (2013.01); *G06T 2207/20221* (2013.01)

(58) Field of Classification Search
None
See application file for complete search history.

(56) References Cited

U.S. PATENT DOCUMENTS

| 2005/0169433 | A1* | 8/2005 | Kay | A61B 6/14 378/168 |
| 2005/0213849 | A1* | 9/2005 | Kreang-Arekul | G06T 3/4038 382/284 |
| 2011/0188726 | A1* | 8/2011 | Nathaniel | G01N 23/04 382/132 |
| 2013/0028379 | A1* | 1/2013 | Nelson | G01N 23/04 378/62 |

* cited by examiner

*Primary Examiner* — Matthew C Bella
*Assistant Examiner* — Brian D Shin
(74) *Attorney, Agent, or Firm* — Lawrence S. Cohen; Brian Billett

(57) ABSTRACT

A multi-pouch container or carrier for imaging plates which includes multiple pockets which are overlapped, in which multiple relatively small plates can be inserted, sequenced and aligned in a defined overlapping such that simultaneously exposed plates in the pockets form overlapped images which can be stitched together by application software to provide a larger variable sized single contiguous image of a region of interest.

36 Claims, 11 Drawing Sheets

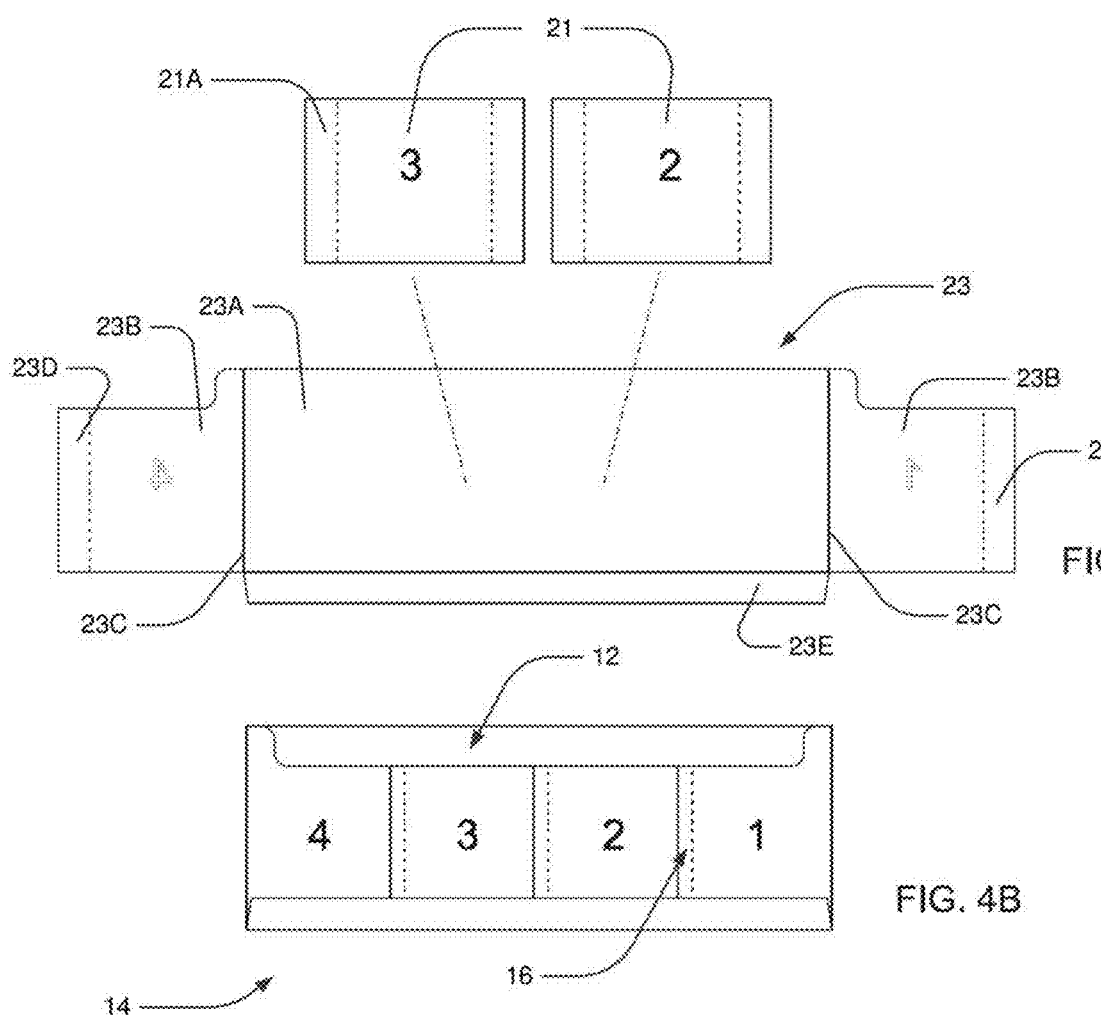

US 10,631,813 B1

MULTI-POCKET CARRIER FOR X-RAY PHOTO-SENSITIVE PLATES AND SYSTEM AND METHOD OF USE

FIELD OF THE INVENTION

This invention relates generally to digital radiography devices and methods.

BACKGROUND

Historically intraoral dental radiography has been based on X-ray film. Typically standard dental X-ray film is limited to sizes that can fit inside a human mouth. Similarly, processing machines for dental X-ray film are generally restricted to single film(s) which are limited to these small standard sizes.

The dental and veterinary fields have been moving toward digital radiography systems which use reusable imaging media, such as Photostimulable Phosphor (PSP) plates. In a typical imaging application, a PSP plate is inserted in a patient's mouth and exposed to X-rays, similarly to standard X-ray film. The exposed PSP plate is then removed from the patient's mouth and "developed" by a laser scanner, whereupon the image on the plate is displayed and stored by a computer. The exposed plate is then erased or reset by a flash of bright light and may be reused. Current systems are typically limited to small standard dental plate sizes. Alternatives for capturing larger radiographic imaging can be expensive and difficult.

SUMMARY

Disclosed are a system and method for containing, holding and aligning an array of overlapping reusable X-ray media for radiography. The disclosed system and method provide the capability to combine the individually captured overlapping images from the PSP plates in the array by digitally stitching together the overlapping digital images into a single contiguous image. The PSP plates can then be processed by stitching so as to provide a continuous image field. This then allows the use of processing and display producing equipment for large areas being X-rayed using the smaller plates in overlapped exposure and being stitched to display the whole larger area.

BRIEF DESCRIPTION OF THE DRAWINGS

FIG. 4A shows an example embodiment for unassembled parts of a 4×1 carrier of overlapping PSP plates.

FIG. 4B shows the assembled 4×1 plate carrier from the unassembled parts in FIG. 4A.

DESCRIPTION

Figure 1:
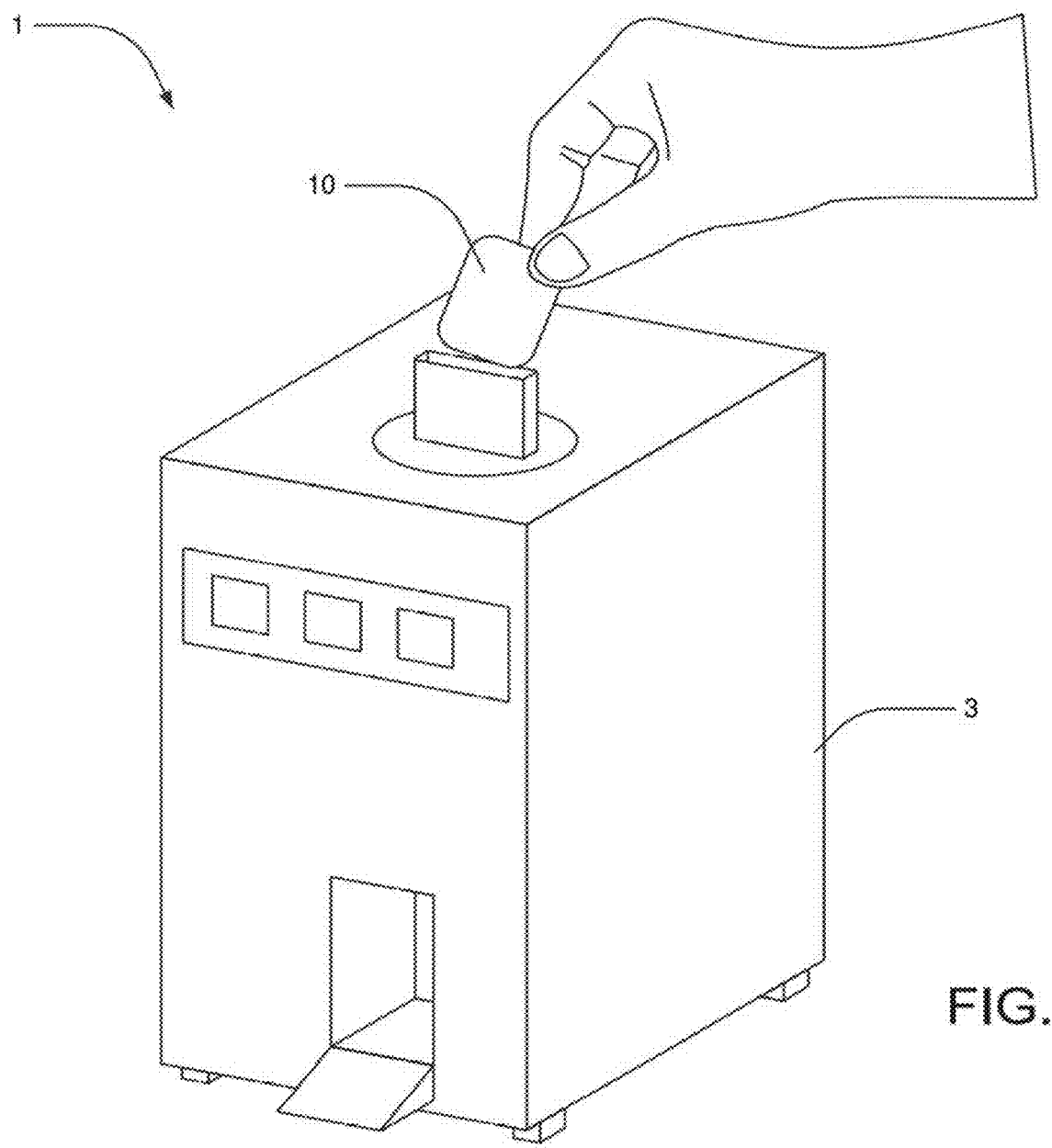
FIG. 1 shows a digital X-ray plate scanner for use in digital radiography that takes PSP plates.

With the advent of reusable image receivers, complications have emerged concerning the size of the reusable media where plate users can only capture a limited area. As these phosphor plates are quite small, and are processed using a small processing device, in many cases, such as in medical, dental and veterinary radiography applications, it might not be possible to capture the whole object of interest in a single field of view or a single image. PSP plates are typically limited to standardized sizes and are incapable of capturing images larger than the size of the plate without requiring purchase of specialized scanners. Large scale processors, however, are very expensive due to their size and specialization.

In certain current Digital Radiographic (DR) imaging solutions, both the X-ray source and flat panel detector (FPD) are moved vertically or horizontally sequentially to acquire multiple images (e.g. of a patient's spine or leg for scoliosis or long bone study for bone alignment, or for other physiological measurements). Clinicians, however, generally prefer a single contiguous image showing "a whole region of interest" for medical study and diagnosis. To simulate this without actually achieving it, a typical effort uses multiple views of an area of interest acquired as multiple images by automatically (synchronously) or manually (asynchronously) moving the sensor and light source with respect to the object of interest.

To solve problems of current radiography systems described briefly above, the disclosed solution uses systems and methods for holding and aligning an array of PSP plates which may be simultaneously exposed to X-rays and then individually and sequentially scanned by a commercial specialized scanner for scanning the plates. Exemplary of such scanners are digital radiography imaging systems using PSP plates, one example being the ScanX Intraoral. Digital PSP Radiography System made by Air Techniques, Inc. of Melville, N.Y. Another example is the Apixia. PSP Scanner made by Apixia, Inc. of Industry, California. In the last stage of the method disclosed, a digital image processor digitally stitches together adjacently overlapping images acquired from the array of exposed PSP media, into a single contiguous image. In contrast to previous methods, the presently disclosed system provides for simultaneously exposing the plates, which minimizing potential differences between overlapping regions of adjacent images and provides additional mechanisms to improve the accuracy of adjacent image stitching. Therefore, in the context where only PSP media and reading equipment is available, a larger area of imagery may be achieved, which would otherwise require the more expensive equipment for reading larger imagery and using larger imagery to be read.

In a typical disclosed embodiment, a physical plate carrier firmly holds an array of plates in adjacent pockets that have an overlapping portion so as to allow the plates held in adjacent pockets to be in an overlapping orientation defining a continuing series of overlapping plates from a minimum of two plates. The carrier is transparent to X-ray light and holds individual adjacent plates in an overlapping orientation. As will be fully described below the overlap can be of side-to-side adjacency or of up-and-down adjacency and in a combined array, of both side-to-side and up-and down adjacency. The extent of the overlapping region of the plates may vary according to the application, the type and/or size of plates used and acceptable plate placement tolerance for the imaging being sought.

The plate carrier may be constructed of plastic, paper or other material suitable for disposable use or more expensive material suitable for reusable use. It is desirable but not essential, that the plate carrier be flexible so as to allow freedom of placement and adjustment to the intended target for the X-ray process. While the plate carrier will have a plurality of the adjacent pockets, in use it may be partially filled or fully filled with an array of X-ray imaging plates. Partial filling of the carrier provides a capability for acquiring an assortment of shaped and sized single contiguous images. A partially filled carrier would in one embodiment have adjacent pockets containing plates in the overlapping orientation, to define a continuing series of adjacent overlapping plates while there are unoccupied pockets outside the continuing series.

Upon the desired arrangement of plates in the pockets, the carrier is put in place for the imaging as desired, the imaging process is executed by operation of the X-ray apparatus thereby to provide the continuous image over a distance, with overlapping imagery in the overlapping regions of the plates.

In typical operation of the disclosed system, an operator removes PSP plates sequentially from the carrier and feeds them to a PSP plate scanner which acquires digital images of the plates sequentially as they are fed into the scanner. The disclosed image processing component may then be configured to automatically stitch together overlapping images in the array according to a detected sequence of images based on the ordinal sequence of detected images or based on detected markers on the plates or based on an inserted order of identifying the image position arrangement to be stitched together for the desired output of a continuing image. The output of the system is the resulting single contiguous radiographic image. With use of a plurality of adjacently oriented plates, by such designation of order on the plates or by designation of order as fed into the scanner, a continuous image field can be obtained as instructed to the processing scanner and therein executing the stitching to have the selected contiguous image.

The digital image stitching software implemented in the disclosed system may utilize a specially developed image processing software, or commercially available software packages or methods and algorithms, which are well known in the art for stitching together overlapping images.

By use of the disclosed plate carrier array, a suitable scanner, and configured image processing, the disclosed system and process uses a relatively small unit scanner to scan and image a relatively larger image field at minimum cost of the hardware. The resulting system components are inexpensive, reusable, and physically small compared to available alternatives for digital radiography of similarly sized targets.

In various embodiments, a reusable imaging media plate, such as a PSP plate, is inserted into a plastic or paper pouch or carrier containing a number of slots which are aligned in order and fit the shape of the imaging plate.

Preferably, one or more of the plate slots in the carrier are shaped and juxtaposed in such a way that they can cover a complete area that will be imaged. The carrier is designed so that individual plates positioned in the carrier overlap along their adjacent edges thereby to provide for overlapping of adjacent plates and of the imagery. The adjacency can be horizontal or vertical and may include both. In one embodiment, the carrier is configured to overlap edges of adjacent plates by approximately 1 mm.

Also provided, in accordance with an embodiment, is a method for holding and aligning multiple imaging plates, including:

inserting the plates into a multi-slot pouch or carrier with overlapping adjacency;

identifying the plates by an identification such as by having sequential numbers printed on the pouch pockets to annotate the number and position of the plates which were inserted into the pouch;

preferably, the imaging plates include reusable X-ray sensitive media such as PSP, wherein exposing the plate includes placing the plate so as to receive X-ray passing through a target for imaging such as so as to produce X-ray images of the target;

using an image processing program to stitch the images together. The specific software will recognize the stitching and will sequentially receive or otherwise identify the adjacent order of exposed image and process accordingly. The overlap regions of adjacent images provided by the carrier allows the image processing application to match identical regions of the images, including potential reference marks. The program can allow for adjacently sequential stitching by adjacent sequential identification of the image plates whether they are inserted for reading by the sequence or by another order but using the adjacently sequential identification or by entry of the order by the user keying it in.

In other applications, calibration is performed to determine the optimal overlap distance of the carrier pockets and adjacent images. As will be seen in more detail below, spatially efficient stitching algorithms are desired in medical X-ray imaging, since a smaller overlap can in some cases be useful to minimize a patient's X-ray dosage. For example, patient dosage can be reduced by reducing the number of images needed to image a particular desired field of view.

Current image processing technology provides a variety of published methodologies and commercial applications for fusing or stitching together multiple images from a single field of view into a single contiguous image. The multiple images can be overlapped in at least three ways. The amount of overlap needed or recommended for successful stitching (fusing) varies between applications. As will be described below, in most applications, sufficient image features must be present in the overlapping image region for the method to compare various mathematical attributes of features in templates selected within the overlapping region. As is shown and explained for FIG. 8 below, to stich adjacent overlapping images, typical image processing algorithms identify matching image features from the overlap region of adjacent images. Thus, when using this methodology, the overlap region of adjacent images must have discernable content. For example, if the overlap region is blank, stitching cannot generally be performed utilizing a feature matching algorithm. In such cases, a less reliable method would be to perform stitching based on the know dimensions of the plate and overlap portion. An alternative to feature matching is to match other non-noise image content which may not be discernable to viewers but may be identifiable and matched by mathematical attributes or patterns of the image pixels in the overlap portion. In some applications, such as some medical or industrial radiographic applications, industry standards or professional practice guidelines may be available which suggest or require overlap dimensions. In other applications, calibration testing may be used to determine sufficient overlap distances. Generally, spatially efficient stitching algorithms are desired for medical X-ray imaging, since a smaller overlap may help minimize the required X-Ray dosage. Thus the methodology minimizes potentially harmful radiation exposure to the patient as well as present care-givers.

In medical applications, Flat Panel Detectors (FPD) are commonly used to capture both high- and low-resolution X-Ray (shadow) images. As previously described, in many cases, such as in medical radiography applications, it might not be possible to capture the whole object of interest in a single field of view or a single image. This is notably the case when the available capture media, such as PSP plates are only available in limited sizes. As has been mentioned, clinicians generally prefer a single image showing "a whole region of interest" for medical study and diagnosis. Yet, because of the large size of some objects of interest, e.g. long bones, or in cases where a very high-resolution image of a small object is required, multiple image acquisition is the only viable option. The device described herein can assist in combining multiple images (e.g. sequences of images) into a single overall image of the region of interest.

Combining or "stitching" multiple images herein refers to the process of substantially joining images of adjacent fields of view which have a some finite overlap region. For typical embodiments, two images are joined at a time; more images can be joined by repeating the process. The portion of the adjacent images which overlap present identical image content and are in many embodiments stitched by matching the overlap image content.

A single contiguous image of interest from multiple acquired images of a given size is an area (region) defined with multiple images made into one. In the context of image stitching, this typically includes part or all of a region within an overlapping area of two images to be stitched. As part of the image stitching method, a template selected from the first window is matched with an image by noting the sequence in which the images were scanned a larger whole image can be generated from smaller ones. This single large image made of smaller images typically include a common area or "overlap region" where the adjacent sides of sequential images overlap each other, as various embodiments are described.

Shown in FIG. 1 is an exemplary prior art PSP plate scanning apparatus 1 for digitizing exposed PSP plates 10. The drawing depicts an Apixia Dental Imaging phosphor plate scanner 3. The use of a simple dental plate scanner such as this extends the benefits of x-ray imaging technology to a variety of applications at low cost using the various disclosed embodiments.

Figure 2:
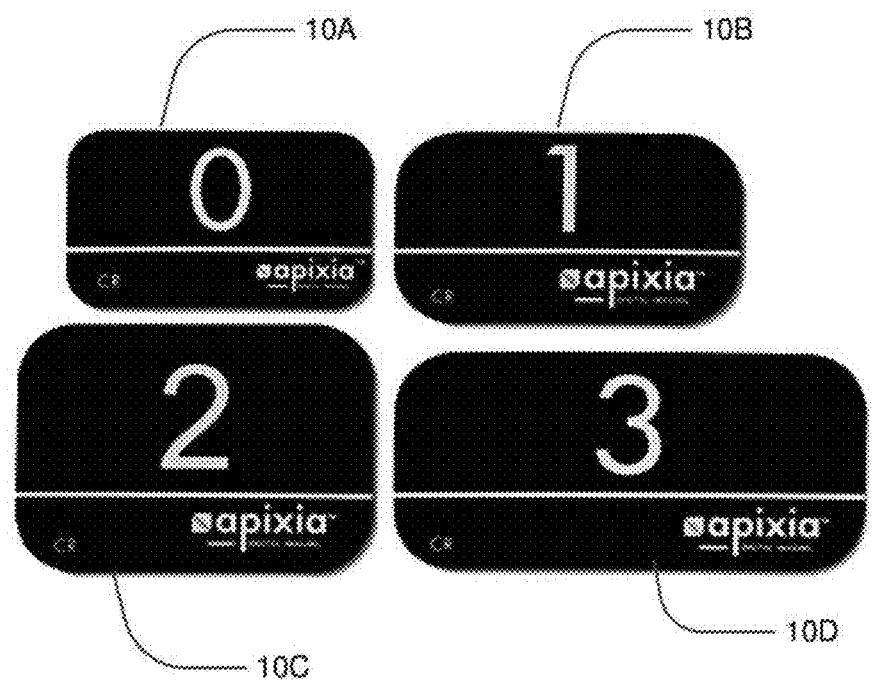
FIG. 2 shows examples of reusable X-ray film plates (PSP plates) suitable for various embodiments.

Shown in FIG. 2 are exemplary prior art phosphor plates in various stock sizes: "0" 10A, "1" 10B, "2" 10C and "3" 10D for these Apixia manufactured phosphor plates. Various embodiments disclosed may use these or other stock PSP plate sizes.

Figure 3:
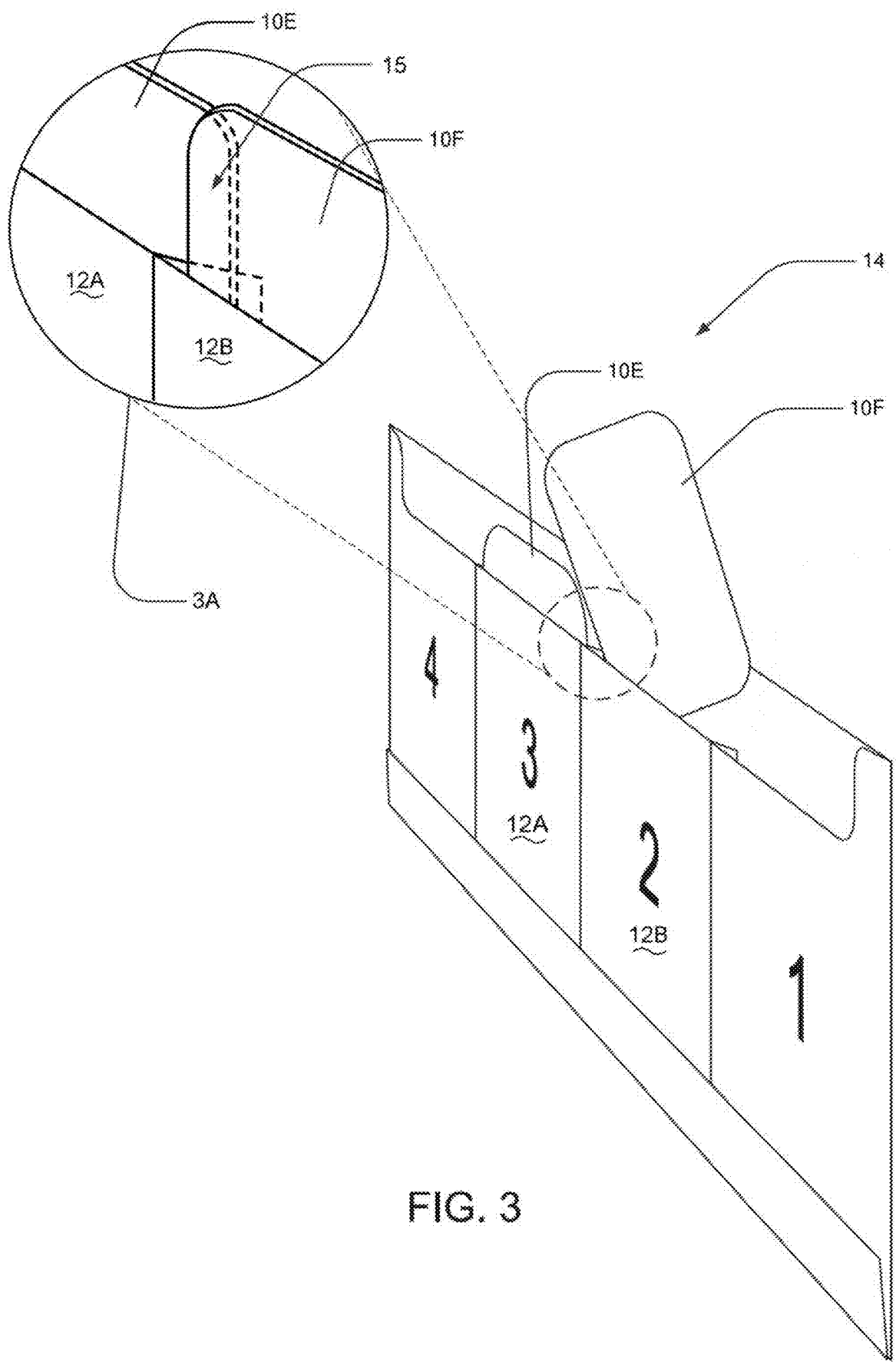
FIG. 3 shows an exemplary embodiment featuring a 4×1 carrier of overlapping PSP plates with an inset drawing 3A of a section showing how the carrier pockets are configured so that adjacent PSP plates in adjacent pockets overlap.

FIG. 3 shows a 4×1 embodiment of the PSP plate carrier 14 from a perspective view. Shown here one can see the PSP plates being inserted at 10F and in place at 10E into the overlapping pockets 12A and 12B. Embodiments include carrier pockets being sized so as to orient the plates in a "portrait" orientation, as shown in FIG. 3, or in a "landscape" orientation. In other embodiments a mix of "portrait" and "landscape" oriented pockets are mixed to configure the plates in a shape optimally covering the "region of interest" to result in the desired image field. An inset drawing 3A is included which shows a zoomed overlap image of overlapping adjacent PSP plates 10 E and 10F after insertion into adjacent carrier pockets 12A and 12B. The plate overlap region 15 (also called a plate overlap dimension) of adjacent plates is also shown in inset 3A.

Figure 4C:
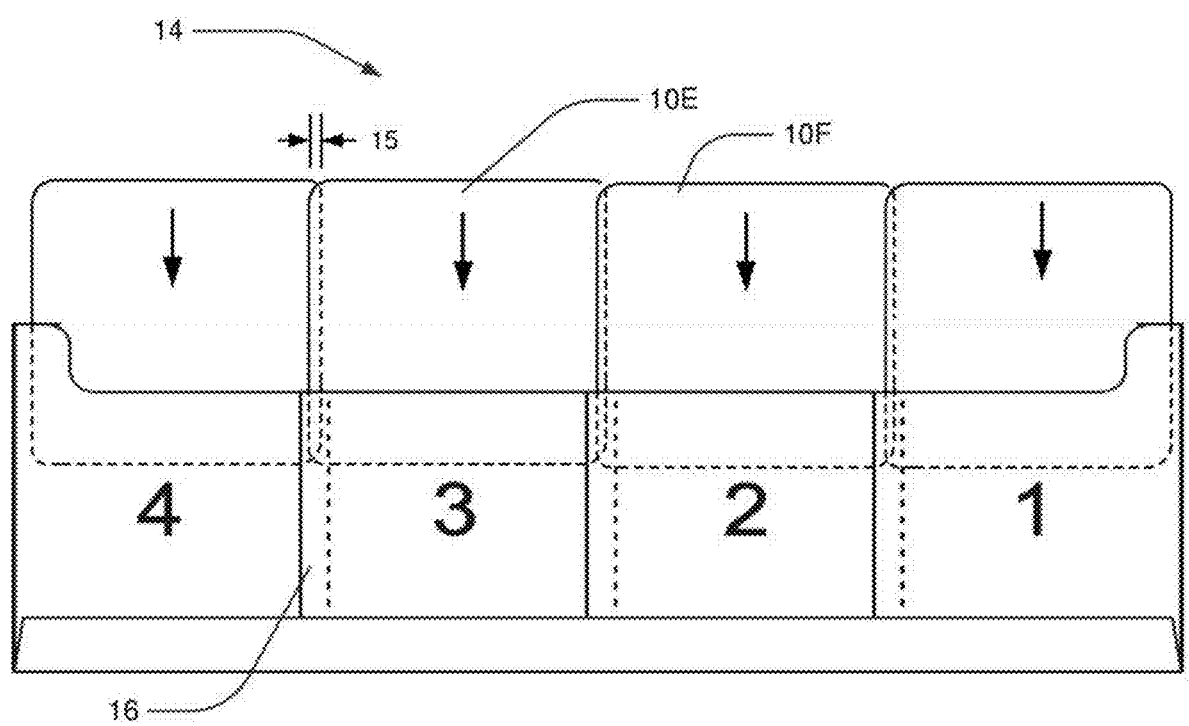
FIG. 4C shows a front view of the assembled 4×1 plate carrier as in FIG. 4B from the unassembled parts in FIG. 4A with partially inserted overlapping plates.

An embodiment for making a 4×1 PSP carrier or pouch having a plurality of laterally extending pockets is shown in FIGS. 4A, 4B, 4C, 4D and 4E. As will be seen the carrier 14 is made by assembly of parts resulting in laterally extending adjacently overlapping pockets, designated as 1, 2, 3 and 4. As seen in FIG. 4A, pockets 2 and 3 that are within the interior expanse of the adjacent pockets are formed with front pocket surfaces 21. The rear pocket surfaces and the end pockets are formed from a single forming piece 23 which has a back surface 23A that forms the back of all the adjacently overlapping laterally extending pockets. At each lateral end of the forming piece 23 are flaps 23B which are to be folded along line 23C to form the front of pockets 1 and 4 with end portions 23D folded along the dotted lines 23E so as to be affixed adhesively to the back surface 23A (seen in 4E) and also having common overlap with the next adjacent pocket, wherein the common overlap is also adhesively hound. The adhesively attached surfaces are shown with the designation AD in FIG. 4E. The adhesive binding can be done by direct application of an adhesive or by the use of double-sided pressure sensitive adhesive tape. A bottom flap 23E is to be folded up to form the bottom of the pockets. The resulting pocket overlap portion is 16 (seen in FIGS. 4B and 4C). FIG. 4B shows the assembled overlapping plate carrier showing the pocket overlap portion 16 providing a plate overlap region 15 (seen in FIGS. 3A and 4C). It can be understood that the fitting of the plates into the pockets will result in some variation of the plate overlap region depending on the fit of the plates into the pocket and on how the plates may be urged into the pocket overlap region.

Therefore it can be understood that in the above description there is a lateral range of adjacent pockets. Each pocket has opposite sides (as in a left side and a right side). Thus, there are end or outer pockets in the lateral range of adjacent pockets, each having opposite sides one of which is exterior to the lateral range of pockets and the other side is interior to the lateral range of pockets. There are interior pockets in the lateral range of pockets also having opposite sides. Therefore, it can be understood that in the lateral range of pockets each of the outer pockets overlaps an adjacent pocket on one lateral side only, the interior side. The interior pockets in the range of pockets laterally overlap adjacent pockets on each of their opposite lateral sides. The range then, has an outer pocket on each end which have a single overlap with an adjacent inner pocket and there are inner pockets which have an overlap with adjacent pockets on each side. It can then be defined that each pocket of a lateral range has an overlap with any adjacent pocket defining a pocket overlap region. As will be described below, when plates are in adjacent pockets they will overlap by an amount defined as the plate overlap region. The lateral range of pockets may be considered a row of pockets.

As shown in FIG. 4B, when assembled the PSP pocket carrier 14 is formed in this embodiment with 4 uniform overlapping calibrated (for equal pocket overlap region) pockets 12. When assembled, the individual pockets overlap such that adjacent plates closely fitting the pockets are overlapping on the adjacent edges of the plates. The overlapping pockets form a pocket overlap region 16 giving a plate overlap region 15 upon insertion of the plates. Given the practicality of construction, it is considered that the dimension of the pocket overlap region is not necessarily the same as the resulting dimension of the plate overlap region, The plate overlap region may have a dimension that is equal to (within practical measurement availability) or less than the dimension of the pocket overlap region.

FIG. 4C shows the carrier 14 as in FIG. 4B with the plates 10 being partially inserted in the overlapping pockets with the resulting plate overlap region 15. It can be understood that the pocket overlap region 16 of the adjacent pockets would be sufficient to allow an actual plate overlap region 15 of the plates. As is shown, the plates overlap in a cascading pattern in this configuration, but that order is not essential. The pocket overlap region 16 of the pockets allows a plate overlap region 15 (also referred to as a plate overlap dimension). As explained below, the plate overlap region 15 causes a resulting image overlap on the adjacently overlapped plates when the imaging on the plates is processed.

Figure 4D:
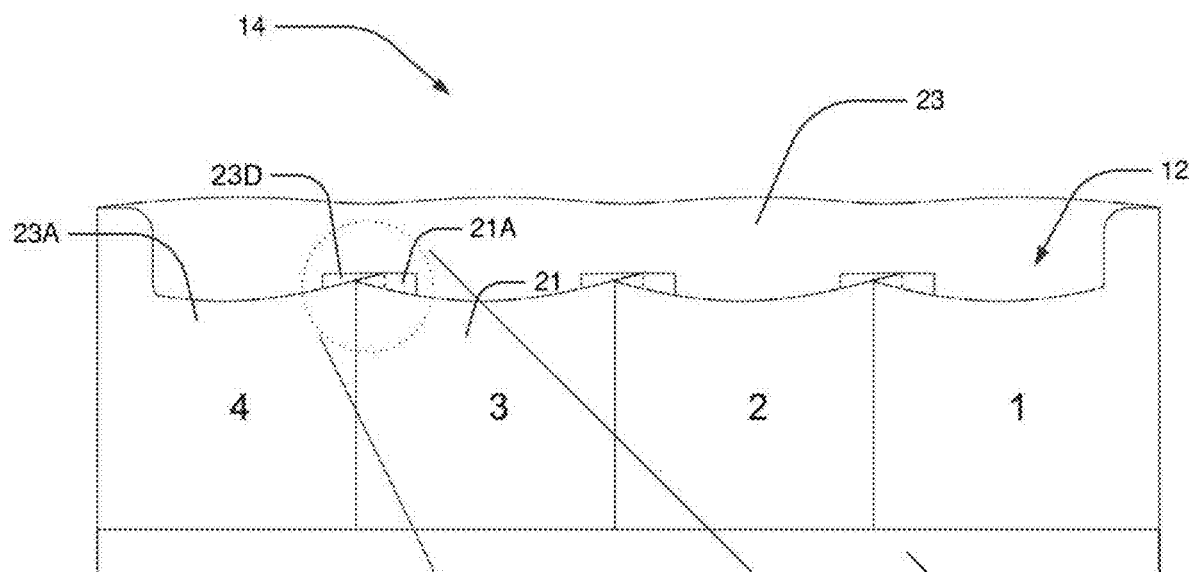
FIG. 4D shows a perspective front view of a 4×1 carrier embodiment with the pockets opened to show interior structure.
Figure 4E:
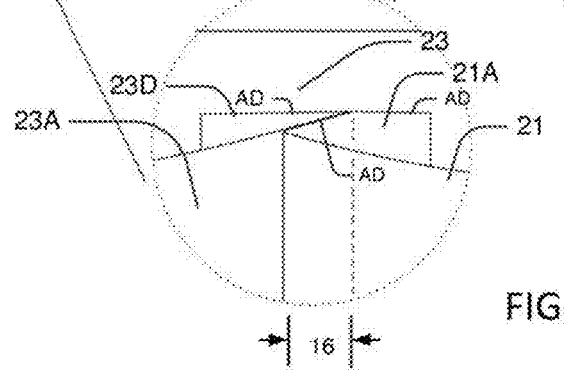
FIG. 4E shows a close-up inset from FIG. 4D showing details of the interior fold and adhesive structure to form the overlapping portion of the pockets.

FIG. 4D is a front view of the carrier structure 14 with the pockets partially open such that the interior fold detail of the carrier pockets is shown. During assembly of the carrier, flaps 23B are folded over along line 23C to form pockets 1 and 4, with the end portion 23D of the flaps 23B folded again along dotted line 23E to be affixed to the back panel 23A of the carrier 23. The next pocket (3) front portion 21 is shown with end portions 21A to be folded back underneath and affixed both to the adjacent pocket and to the hack panel 23.

The close-up inset 4F, shows a detailed view of the pocket interior fold structure, in particular that the adjacent pocket (3) end portion 21A is affixed both to the front of panel (4) 23A and the back panel 23 to form the overlapping structure for adjacent plates. The surface portions that are adhered together are indicated as AD whereby end portion 23D is adhered to the back panel 23A and a portion of the end portion 21A of pocket 21 is adhered to the front of pocket 4 (23A) and a portion of flap 21A is adhered to the back panel 23A thereby providing the overlap region 16 adjacently in the adjacent pockets.

Figure 5A:
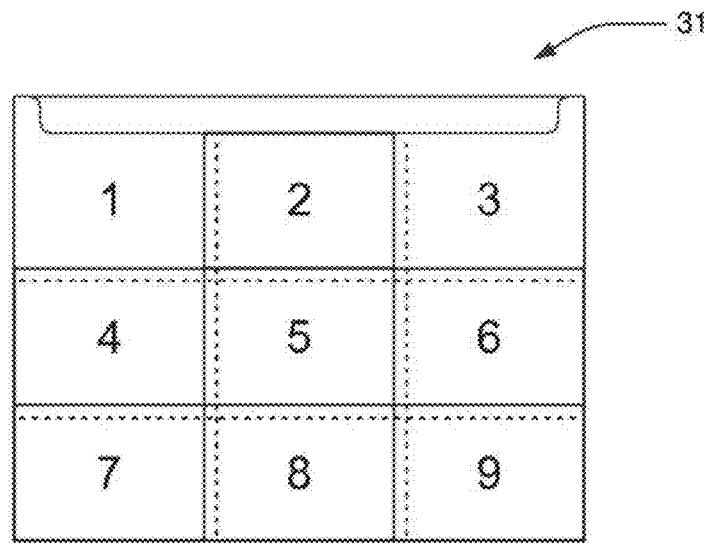
FIG. 5A shows an exemplary embodiment of a 3×3 PSP plate carrier.
Figure 5B:
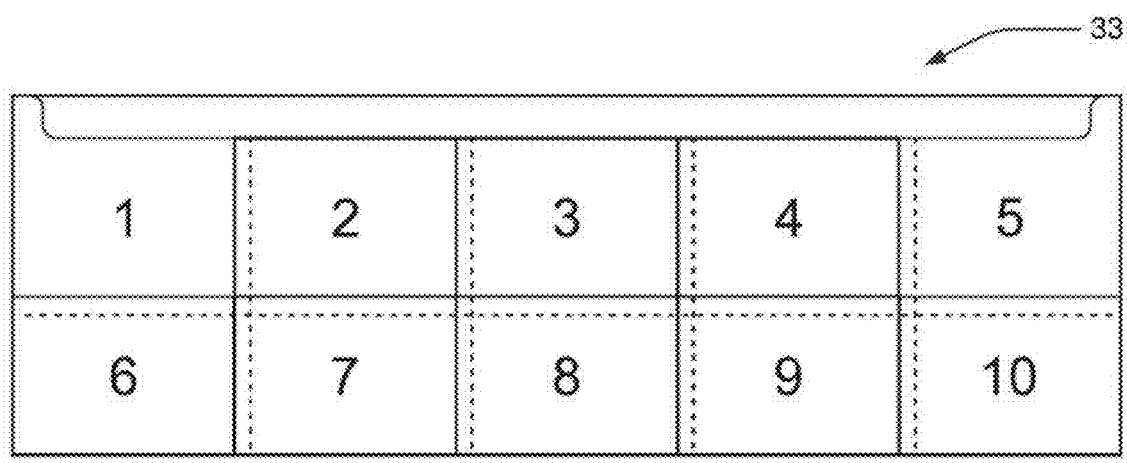
FIG. 5B shows a 5×2 PSP plate carrier.

Alternative embodiments include arrangements and orientations of the aforementioned PSP plates using different types and dimensions of PSP plates and different dimensions to appropriately record X-ray images of the object being X-rayed. For example in FIG. 5A a 3×3 (3 rows and 3 columns) array PSP plate carrier 31 is shown which is appropriate for similarly sized round or square X-ray targets. FIG. 5B shows a 2×5 (2 rows and 5 columns) array PSP plate carrier 33 which is appropriate for similarly sized elongated X-ray targets. Embodiments include all possible two-dimensional arrays of PSP plates, including arrays which may be missing row and column pocket positions, but form contiguous geometric shapes. The definitions of rows and columns are derived from each pocket being open to receive a plate at its top. Thus an arrangement of laterally adjacent pockets open at the top of each pocket will define a row and an arrangement of vertically adjacent pockets open at the top will define a column. Of course in a particular array, a pocket can be in both a row and a column.

Figure 6:
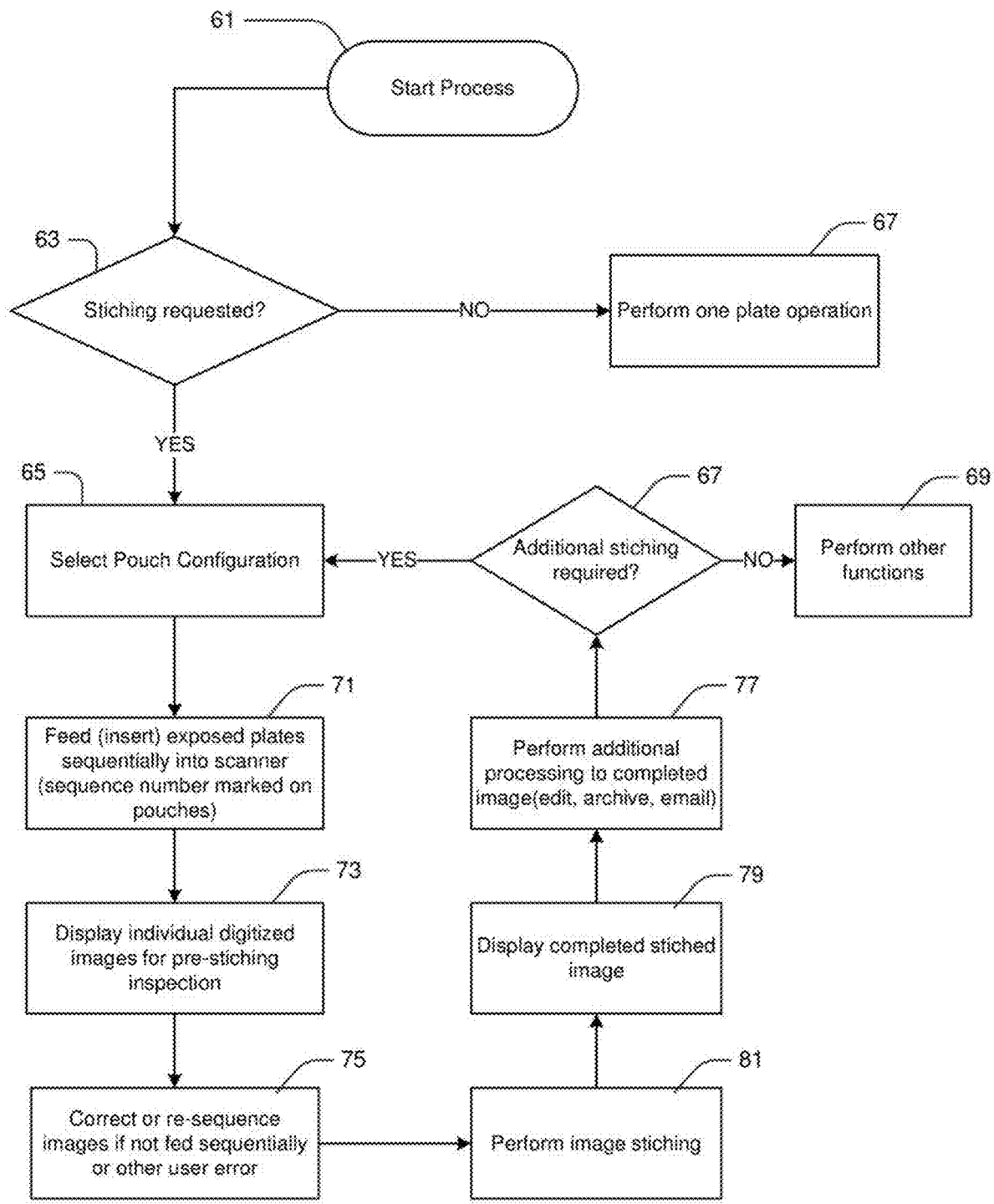
FIG. 6 is a flow chart of a typical embodiment process for utilizing a multi-pouch PSP plate carrier to capture a contiguous large radiography image from an array of overlapping PSP plate images from the plates held in the overlapping array.

FIG. 6 depicts a flow chart detailing an exemplary process for utilizing the disclosed PSP multi-plate imaging system. The flow chart begins by starting the process 61 as initiation of a multi-plate digitizing process that will enable requesting of the stitching process 63. If a multi-plate digitizing process is not chosen, a single plate is digitized to complete the process 67. If multi-plate processing is indicated, the multi-plate configuration (1×2, 2×2, 1×3, 2×3, 3×3 . . . W×L) is input by a user 65. In alternative embodiments, configuration is automatically detected by marking or other indicia on the plates. Then exposed plates are fed in sequence to the scanner 71. In other embodiments, plates are stacked in an automatic feeder and may be sequenced according to plate marking or indicia or by input by the user as the plates are inserted. In various embodiments the user is shown the individual images to inspect 73 and if necessary re-sequence 75. In other embodiments, re-sequencing is performed automatically by image analysis or according to identified plate marking or indicia. Next, the individual scan plate images are "stitched" together 81 utilizing one of many techniques known in the art. Numerous techniques are known in the art including off the shelf commercial products like AutoStitch, or the use of an open-source algorithm or code for performing stitching 81. In various embodiments, image registration marks on the PSP or object features identified after digitization may be utilized to facilitate image stitching. Once stitching is performed, the contiguous image is displayed to the user for verification or diagnosis 79. The final image is then available for further processing including the user initiated or automatic communication to a recipient by email, automatic or manual editing or image optimization 77. Then additional stitching of the acquired plate images may be performed 65 or scanning of additional plates may continue 69.

Figure 7:
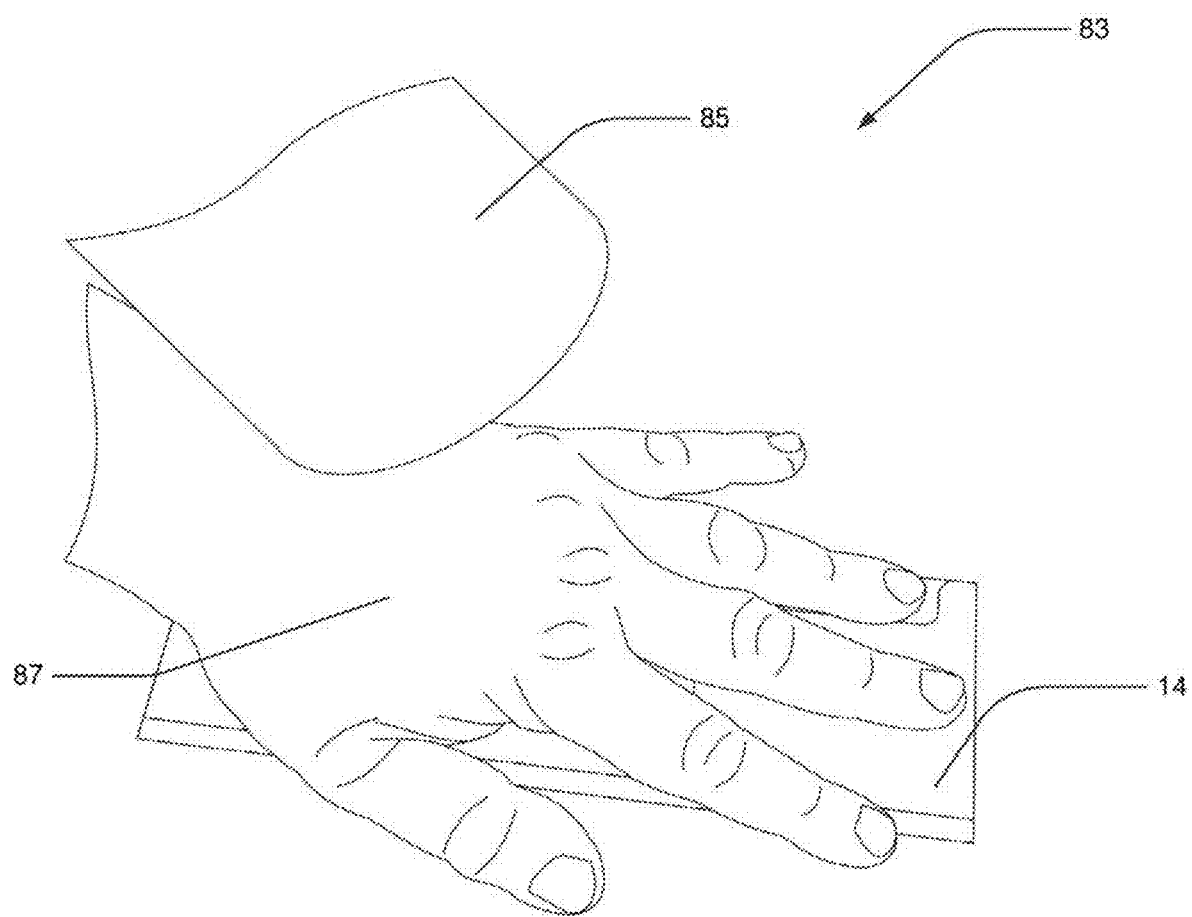
FIG. 7 shows an exemplary setup for using a multi-pouch PSP plate carrier which holds unexposed plates and an X-ray source directed to a person's hand.

FIG. 7 shows a typical set-up 83 for exposing multi-plate PSP arrays. In the shown set-up, an X-ray source (tube) 85 is positioned over the targeted object 87, which in the shown embodiment setup is a hand. In this exemplary set-up, a 1×4 multi-plate array 14 is positioned below the target object. In various alternative embodiments, the X-ray source may be hand held.

Figure 8:
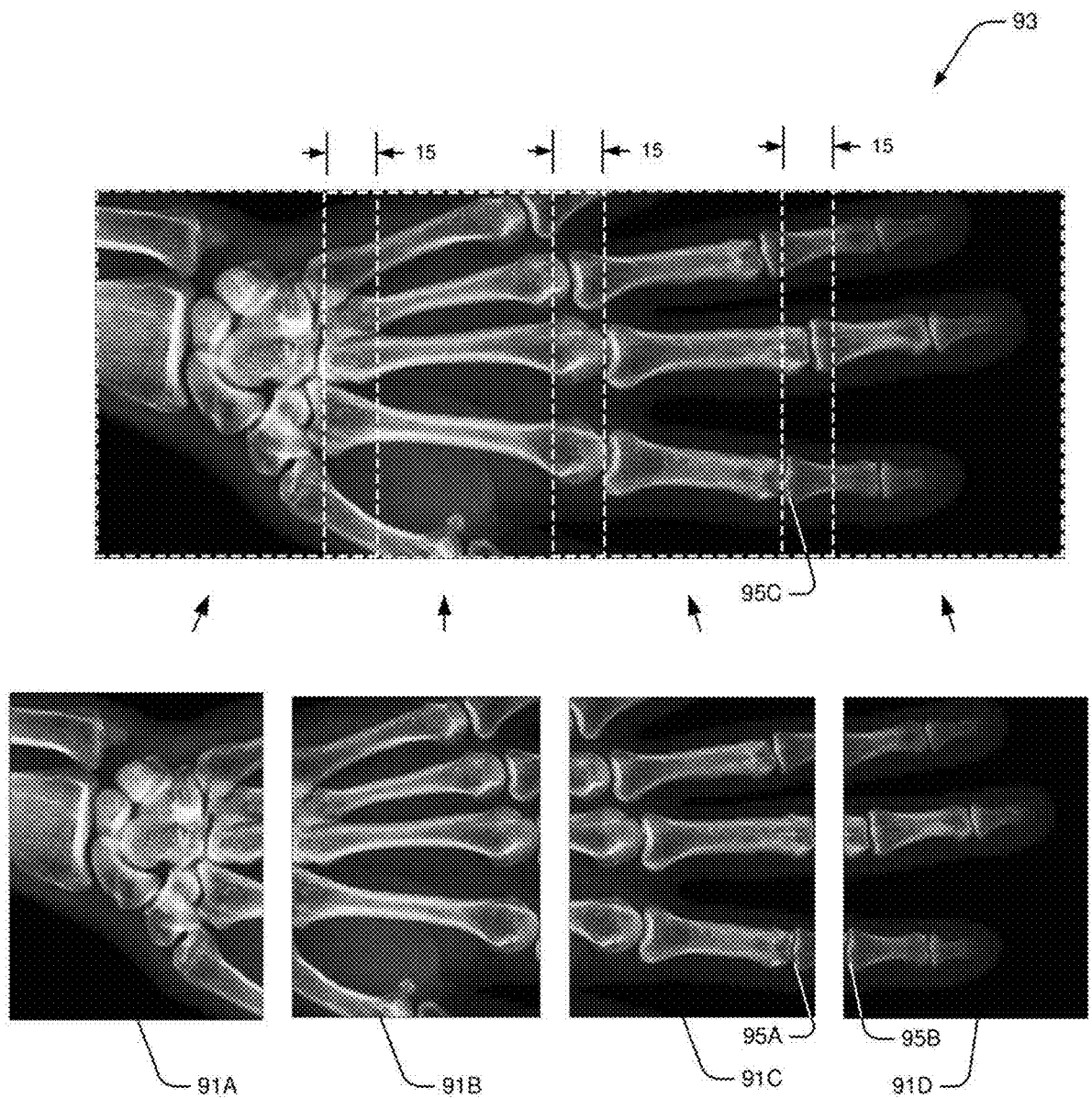
FIG. 8 shows exemplary images digitized from PSP plates exposed in a 4×1 plate carrier array before and after digitally stitching the images into a contiguous single image from overlapping plates.

In FIG. 8 digitized X-ray images from exemplar PSP multi-plate carrier in FIG. 7 are shown 91A, 91B, 91C, and 91D. After digitizing the overlapping individual plate images shown, the system stitches the plate images together according to a system algorithm resulting in a contiguous image 93 suitable for radiology diagnosis, screening or mechanical inspection. Shown in the top image 93 are the plate overlap regions 15 of adjacent images which are stitched together. The plate overlap region 15 to be allowed by the adjacent pocket structure is determined according to the specified embodiment application including the expected content density of the image. For example, in the shown images, which are overlapping X-ray images of a human hand, the content of the subject of the image (a hand) extends continuously across all the plates. Thus, variations of the image content will exist across the overlapping regions and an overlapping region could be close to zero and could be based on tolerance between the plates and their carrier pockets. In various embodiments, the image stitching algorithm uses detected image features within corresponding overlap regions to align and stitch adjacent images. As an example, the knuckle joint gap 95A between the index finger medial phalange and proximal phalange is identified in the right-side overlap region of image 91C. The gap 95B is also identified in image 91D in the left-side overlap region. Once stitching is completed, the gap 95C can be seen in the overlap region of the final contiguous image 93.

Figure 9:
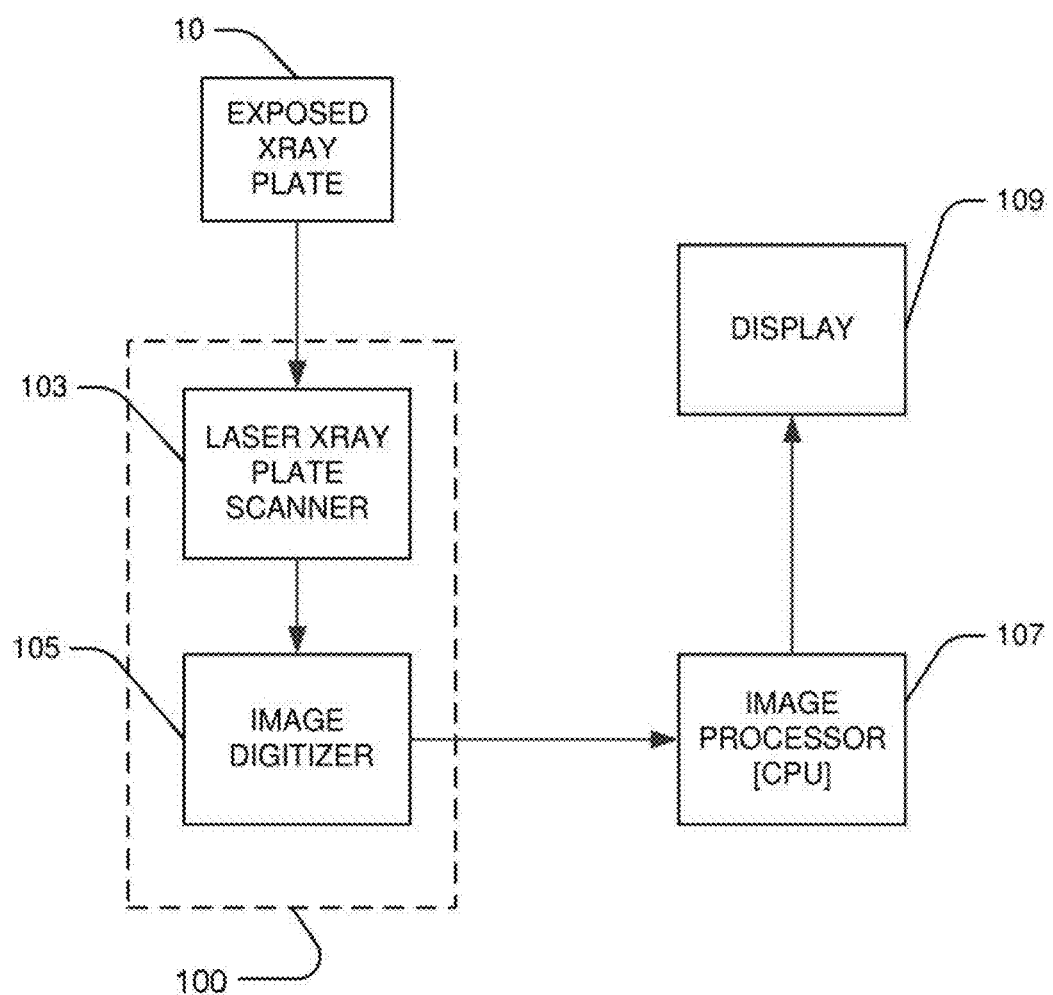
FIG. 9 shows a component diagram of an exemplary system which includes the digitizing scanner, image processor and display.

FIG. 9 shows an exemplary component configuration which includes various hardware components performing the functions outlined above and in FIG. 6. Reusable PSP plates 10 such as those shown in FIG. 2 which have been exposed to a target are fed into a scanning and digitizing apparatus 100 which may be a commercially available scanning machine. Appropriate plate scanner/digitizers commonly use laser scanners 103 to scan the exposed plate and a digitizing component 105 to encode the image scanned from the plate. A set of images digitized from plates which have been simultaneously exposed while contained in a carrier such as those disclosed herein, are then "stitched" together by the image processing component 107 which is typically performed by a central processing unit or a graphics processing unit of a computer. Contiguous images which have been stitched together from individual exposed plate scanned and digitized images may then be displayed, typically on a computer monitor 109 to a diagnostician or inspector.

In alternative embodiments, registration marks made of X-ray material of limited absorbing properties may be affixed to or printed on the front of the plate carrier positioned within each of the overlap regions. The registration marks, which may be of many forms such as a dot or cross, absorb a limited amount of X-ray radiation when the plates are exposed. This results in registration mark "shadows" being recorded on both plates underneath the mark. The image processor which performs the stitching detects the registration mark in the overlap region of adjacent images and aligns the individual images for stitching based on the mark position. Once all the images are stitched together, in some embodiments, further image processing is performed to remove the marks from the final image based on the expected resulting "shadow" grey-scale impact. For example if the mark is expected to lighten the final image by 50/256 grey levels in an 8-bit grey-scale image, the final image pixels forming the mark in the image would be darkened by the same amount to effectively "erase" the mark from the image. In alternative embodiments, the registration marks on the front of the carrier may be individually distinct from each other to indicate the position of the mark in the multi-plate array. In this embodiment, the image processor is configured to detect the various mark types, identify the position of those marks in the array, and automatically place the individual plate images during stitching. Thus, the image processor in this embodiment is capable of stitching the images regardless of the sequence in which the images were scanned, and without the assistance of an operator. Similarly, the image processor may be configured to flip or mirror individual images which may have been incorrectly scanned (upside down or reversed). Similarly as described above, the resulting registration marks on the stitched image may be "erased" by image processing to remove the mark.

In various embodiments, the multi-plate carrier and image processor may be utilized for radiographic imaging of veterinary patients or the inspection of mechanical components such as fasteners for internal fractures. The application of the disclosed technology should not be limited to the examples presented here.

The routines and/or instructions that may be executed by the one or more processing units to implement embodiments of the invention, whether implemented as part of an operating system or a specific application, component, program, object, module, or sequence of operations executed by each processing unit, will be referred to herein as "program modules", "computer program code" or simply "modules" or "program code." Generally, program modules may include routines, programs, objects, components, logic, data structures, and so on that perform particular tasks or implement particular abstract data types. Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. Given the many ways in which computer code may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The flowcharts, block diagrams, and sequence diagrams herein illustrate the architecture, functionality, and operation of possible implementations of systems, methods, and computer program products according to various embodiments of the present invention. In this regard, each block in a flowchart, block diagram, or sequence diagram may represent a segment or portion of program code, which comprises one or more executable instructions for implementing the specified logical function(s) and/or act(s). Program code may be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the blocks of the flowcharts, sequence diagrams, and/or block diagrams herein. In certain alternative implementations, the functions noted in the blocks may occur in a different order than shown and described. For example, a pair of blocks described and shown as consecutively executed may be instead executed concurrently, or the two blocks may sometimes be executed in the reverse order, depending upon the functionality involved. Each block and combinations of blocks can be implemented by special purpose hardware-based systems that perform the specified functions or acts, or combinations of special purpose hardware and computer instructions.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, the embodiments of the invention may be used in conjunction with other machine vision applications for measuring orientation and rotation of spherical or hemispherical objects including objects which may be inherently or deliberately marked with great circles or virtual versions of such markings may be inferred from other inherent features or markings on the object. The invention in its broader aspects is therefore not limited to the specific details, representative methods, and illustrative examples shown and described. Accordingly, departures may be made from such details without departing from the spirit or scope of applicant's general inventive concept.

The invention claimed is:

1. A method for acquiring a contiguous digital radiological image from a plurality of X-ray sensitive plates comprising:
   placing the plurality of X-ray sensitive plates in a multi-plate carrier wherein the multi-plate carrier has a plurality of X-ray plate pockets configured in a flat two-dimensional array configuration wherein each pocket adjacently overlaps at least one adjacent pocket by an overlap distance to define a pocket overlap portion, and is configured to hold the plurality of X-ray sensitive plates in the pockets in adjacent overlap in the pocket overlap portion; wherein in the pocket overlap portion each of the plurality of X-ray sensitive plates overlap a region of an adjacent X-ray sensitive plate to define a plate overlap region also referred to as a plate overlap dimension for the adjacently overlapped region;
   exposing the plurality of adjacently overlapped X-ray sensitive plates in the multi-plate carrier from an X-ray source simultaneously for radiological imaging of an object;
   digitizing in a sequence according to position on the multi-plate carrier each of the plurality of exposed X-ray sensitive plates, wherein a sequence of digital images is created having an image overlap resulting from the plate overlap region;
   stitching the sequence of digitized images together by digital image processing into the contiguous digital radiological image.

2. The method of claim 1 wherein the X-ray sensitive plates are re-usable phosphor plates.

3. The method of claim 1 wherein the multi-plate carrier is configured to hold the X-ray sensitive plates in a carrier having an array of overlapping adjacent pockets with overlapped pocket portions defining adjacent pocket overlap portions allowing the X-ray sensitive plates upon being inserted into the adjacent pockets to have the plate overlap region with adjacent plates having the plate overlap region.

4. The method of claim 1 wherein the contiguous digital radiological image is a medical X-ray image.

5. The method of claim 1 wherein the contiguous digital radiological image is a veterinary X-ray image.

6. The method of claim 1 wherein the contiguous digital radiological image is a inanimate object inspection X-ray image.

7. A system for acquiring a contiguous digital radiological image comprising:
   a plurality of X-ray sensitive plates;
   a multi-plate carrier comprising a series of adjacent pockets whereby the adjacent pockets are in an overlapping configuration such that a portion of a pocket is overlapped with a portion of an adjacent pocket defining a pocket overlap portion wherein the multi-plate carrier is configured to hold the plurality of X-ray sensitive plates wherein each of the plurality of X-ray sensitive plates overlap to define a plate overlap region of adjacent X-ray sensitive plates, wherein the plurality of X-ray sensitive plates in the multi-plate carrier are exposed to X-ray source simultaneously for radiological imaging of an object;
   a radiological plate scanner wherein the radiological plate scanner is configured to receive and digitize each of the exposed plates and to identify the sequential adjacency of the plurality of X-ray sensitive plates according to position on the multi-plate carrier and wherein a sequence of digital images is created in the order of position on the multi-plate carrier; and
   a digital image processor wherein the digital image processor is configured to stitch the sequence of digitized images together by digital image processing into the contiguous digital radiological image.

8. The system of claim 7 wherein the sequential adjacency of the exposed plates is determined by the radiological plate scanner selected from the group; by the order in which the plates are received in the plate scanner, by an indicia of readable imagery on each plate that identifies the overlap order by a digitizer coding on each plate that identifies the overlap order.

9. The system of claim 7 wherein the X-ray sensitive plates are re-usable phosphor plates.

10. The system of claim 7 wherein the multi-plate carrier is configured to hold the X-ray sensitive plates in a lateral extent.

11. The system of claim 7 wherein the multi-plate carrier is configured to hold the X-ray sensitive plates in a rectangular array.

12. The system of claim 7 wherein the contiguous digital radiological image is a medical X-ray image.

13. The system of claim 7 wherein the contiguous digital radiological image is a veterinary X-ray image.

14. The system of claim 7 wherein the contiguous digital radiological image is an inanimate object inspection X-ray image.

15. A multi-plate carrier for holding a plurality of X-ray sensitive plates comprising:
   a carrier backing;
   a plurality of X-ray plate pockets, wherein the X-ray plate pockets are configured in a flat two-dimensional rectangular array configuration comprising at least one lateral row of the X-ray plate pockets, wherein the pockets are fixed on the carrier backing wherein the X-ray plate pockets adjacently overlap each other by an overlap distance to define a pocket overlap portion,
   whereby the multi-plate carrier is configured to hold the plurality of X-ray sensitive plates in the pockets adjacently to enable a plate overlap region whereby simultaneously exposed plates held on the carrier may be digitally stitched together by an image processing device to form a contiguous radiological image.

16. The multi-plate carrier of claim 15 wherein each of the plurality of X-ray plate pockets have identical dimensions which are configured to hold a standard sized commercially available intra-oral radiographic film plate under ISO 3665.

17. The multi-plate carrier of claim 15 wherein the flat two-dimensional array also comprises at least one vertical column of the X-ray Plate pockets.

18. The multi-plate carrier of claim 15 wherein a dimension combination of the flat two-dimensional rectangular array comprises a row lateral dimension and a column dimension chosen from: one by two, two by one, one by three, three by one, one by four, four by one, one by five, five by one, two by two, two by three, three by two, two by four, four by two, two by five, five by two, three by three, three by four, four by three, three by five, five by three, four by four, four by five, five by four, and five by five.

19. The multi-plate carrier of claim 15 wherein the multi-plate carrier is reusable.

20. A system for acquiring a contiguous digital radiological image from a plurality of X-ray sensitive plates comprising:
   a multi-plate carrier being made of flexible X-ray transparent material comprising a series of adjacent pockets whereby the adjacent pockets are in an overlapping configuration such that a portion of a pocket is overlapped with a portion of an adjacent pocket defining a pocket overlap portion wherein the multi-plate carrier is configured to hold the plurality of X-ray sensitive plates in selected adjacent pockets wherein each of the plurality of X-ray sensitive plates overlap a region of one or more adjacent X-ray sensitive plates, wherein the plurality of X-ray sensitive plates in the multi-plate carrier are exposed to X-ray source simultaneously for radiological imaging of an object and the overlap region is commonly exposed;

a radiological plate scanner wherein the radiological plate scanner is configured to digitize a sequence of the plurality of X-ray sensitive plates according to position on the multi-plate carrier wherein a sequence of digital images is created wherein the overlap region of the plates is identified; and a digital image processor wherein the digital image processor is configured to stitch the sequence of digitized images together using a single image portion of the overlap region by digital image processing into the contiguous digital radiological image.

21. The system of claim 20 wherein the X-ray sensitive plates are re-usable phosphor plates.

22. The system of claim 20 wherein the multi-plate carrier is configured to hold the X-ray sensitive plates in a rectangular array.

23. The system of claim 20 wherein the contiguous digital radiological image is a medical X-ray image.

24. The system of claim 20 wherein the contiguous digital radiological image is a veterinary X-ray image.

25. The system of claim 20 wherein the contiguous digital radiological image is an inanimate object inspection X-ray image.

26. A method for acquiring a contiguous digital radiological image from a plurality of X-ray sensitive plates comprising;

providing a multi-plate carrier having a plurality of pockets that are in a two dimensional array in which each pocket adjacently overlaps at least one adjacent pocket defining a pocket overlap portion;

placing the plurality of X-ray sensitive plates in selected pockets of the plurality of pockets such that each plate occupies a pocket overlap portion in common with at least one other plate so that each plate has a plate overlap region with the least one other plate thereby defining a plurality of adjacently overlapped X-ray sensitive plates in the multi-plate carrier;

exposing the plurality of adjacently overlapped X-ray sensitive plates in the multi-plate carrier to an X-ray source for radiologically imaging an object;

digitizing each of the plurality of exposed X-ray sensitive plates and being identified in their relative position in the multi-plate carrier, wherein a sequence of digital images is created having an image overlap resulting from the plate overlap region;

stitching the sequence of digitized images together by digital image processing into the contiguous digital radiological image.

27. The method of claim 26, wherein exposing the plurality of adjacently overlapped X-ray sensitive plates in the multi-plate carrier to an X-ray source occurs as a single simultaneous exposure of the plurality of adjacently overlapped X-ray sensitive plates.

28. The method of claim 26, wherein the contiguous digital radiological image is a veterinary X-ray image.

29. The method of claim 26, wherein the contiguous digital radiological image is a inanimate object inspection X-ray image.

30. The method of claim 26 wherein the contiguous digital radiological image is a medical X-ray image.

31. The method of claim 26 wherein the two-dimensional array comprises at least one lateral row of the plurality of pockets.

32. The method of claim 26 wherein the two-dimensional array comprises at least one vertical column of the plurality of pockets.

33. The method of claim 26 wherein the two-dimensional array is selected from the group consisting of;
a single lateral row and a plurality of vertical columns,
a plurality of lateral rows and a plurality of vertical columns
a plurality of lateral rows and a single vertical column and
a single lateral row and a single vertical column.

34. A method for acquiring a contiguous digital radiological image from a plurality of X-ray sensitive plates comprising:

placing the plurality of X-ray sensitive plates in a multi-plate carrier wherein the multi-plate carrier is configured to hold the plurality of X-ray sensitive plates in adjacent overlap; wherein each of the plurality of X-ray sensitive plates overlap a region of an adjacent X-ray sensitive plate to define a plate overlap region also referred to as a plate overlap dimension for the adjacently overlapped region;

exposing the plurality of adjacently overlapped X-ray sensitive plates in the multi-plate carrier from an X-ray source simultaneously for radiological imaging of an object;

digitizing in a sequence according to position on the multi-plate carrier each of the plurality of exposed X-ray sensitive plates, wherein a sequence of digital images is created having an image overlap region resulting from the plate overlap region;

stitching the sequence of digitized images together by digital image processing into the contiguous digital radiological image;

wherein the multi-plate carrier is configured to hold the X-ray sensitive plates in a carrier having an array of overlapping adjacent pockets with overlapped pocket portions defining adjacent pocket overlap portions allowing the X-ray sensitive plates upon being inserted into the adjacent pockets to have the plate overlap region with adjacent plates having the plate overlap region; and wherein the array of overlapping adjacent pockets may be configured as either or both laterally extending adjacent pockets and vertically extending adjacent pockets.

35. A method for acquiring a contiguous digital radiological image from a plurality of X-ray sensitive plates comprising:

placing the plurality of X-ray sensitive plates in a multi-plate carrier wherein the multi-plate carrier is configured to hold the plurality of X-ray sensitive plates in adjacent overlap; wherein each of the plurality of X-ray sensitive plates overlap a region of an adjacent X-ray sensitive plate to define a plate overlap region also referred to as a plate overlap dimension for the adjacently overlapped region;

exposing the plurality of adjacently overlapped X-ray sensitive plates in the multi-plate carrier from an X-ray source simultaneously for radiological imaging of an object;

digitizing in a sequence according to position on the multi-plate carrier each of the plurality of exposed X-ray sensitive plates, wherein a sequence of digital images is created having an image overlap region resulting from the plate overlap region;

stitching the sequence of digitized images together by digital image processing into the contiguous digital radiological image;

wherein the multiple plate carrier is constructed of flexible X-ray transparent material comprising;

a first member having a continuous length defining a back of a plurality of laterally contiguous pockets and having at its lateral ends additional portions allowed to be folded to form the outer side of lateral end pockets and having a flap along its bottom allowed to be folded to form the bottom of the laterally extending pockets;

additional members formed to extend between the end pockets to form the laterally extending pockets and adjacent pockets having an overlapping portion to define a pocket overlap portion.

36. A multi-plate carrier for carrying a plurality of X-ray sensitive plates in overlapping configuration of adjacent plates comprising;

the carrier being made of flexible X-ray transparent material and comprising a series of adjacent pockets whereby the adjacent pockets are in an overlapping configuration such that a portion of a pocket is overlapped with a portion of an adjacent pocket wherein the carrier is selected from the group consisting of;

a series of laterally adjacent pockets having adjacent overlap portions where they overlap, and a series of laterally adjacent pockets and vertically adjacent pockets having adjacent overlap portions where they overlap.

\* \* \* \* \*